(12) United States Patent
Wang

(10) Patent No.: US 7,430,275 B2
(45) Date of Patent: Sep. 30, 2008

(54) METHOD AND APPARATUS FOR MEASURING THE DIAMETER OF A STEEL REINFORCEMENT ROD IN CONCRETE

(75) Inventor: Chung-Yue Wang, Taipei (TW)

(73) Assignee: National Central University, Taoyuan (TW)

(*) Notice: Subject to any disclaimer, the term of this patent is extended or adjusted under 35 U.S.C. 154(b) by 728 days.

(21) Appl. No.: 11/008,976

(22) Filed: Dec. 13, 2004

(65) Prior Publication Data
US 2006/0126784 A1    Jun. 15, 2006

(51) Int. Cl.
G01N 23/04    (2006.01)
G01B 15/02    (2006.01)
(52) U.S. Cl. .................. 378/56; 378/57; 378/58; 378/163
(58) Field of Classification Search ........... 378/56–58, 378/163
See application file for complete search history.

(56) References Cited

U.S. PATENT DOCUMENTS

| 4,550,255 | A | * | 10/1985 | Sve et al. ................ 250/359.1 |
| 5,210,783 | A | * | 5/1993 | Wallace ..................... 378/207 |
| 5,828,723 | A | * | 10/1998 | Mariscotti .................... 378/58 |
| 5,864,601 | A | * | 1/1999 | Cattorini et al. .............. 378/59 |
| 6,658,089 | B1 | * | 12/2003 | Mohr et al. ................. 378/162 |

* cited by examiner

Primary Examiner—Edward J. Glick
Assistant Examiner—Thomas R Artman
(74) Attorney, Agent, or Firm—Troxell Law Office, PLLC

(57) ABSTRACT

The present invention is for measuring the diameter of a steel reinforcement rod in a concrete. Therein, a comparing rod is deposed outside of the construction and is corresponding to the steel rod to make the magnification rates of the steel rod and the comparing rod be the same. Then, the comparing rod and the steel rod are irradiated by a radioactive-ray source. And, then, a display is provided to show images of the rods to evaluate the size and the defect of the steel rod by the size and the shape of the comparing rod, so that the examination accuracy can be greatly improved and the examination result can be a reference for evaluating the construction safety.

7 Claims, 4 Drawing Sheets

METHOD AND APPARATUS FOR MEASURING THE DIAMETER OF A STEEL REINFORCEMENT ROD IN CONCRETE

FIELD OF THE INVENTION

The present invention relates to a method and an apparatus for measuring; more particularly, relates to examining the size and the defects of a reinforcement steel for evaluating the safety of a construction.

DESCRIPTION OF THE RELATED ART

One prior art now commonly used for measuring the diameter of a steel rod in a concrete is Eddy-current testing, where the Eddy-current effect is monitored to measure the diameter. Yet, when using, the gap between steel rods needs to be large (ex. when the thickness of the protecting concrete of the steel rod is 5 cm, the gap between steel rods needs to be above 14 cm). Besides, the steel rod measured is not to be crossed by another steel rod to prevent from electromagnetic interference. As a result, there are quite a lot limitations, so it is not suitable on actual use.

As shown in FIG. 3 and FIG. 4, another prior art comprises a U-shaped magnet yoke 5 with a coil, a magnetic field 6 and a straight-line path 7, where two ends 8,9 of the straight-line path 7 are located at two ends of the U-shaped magnet yoke 5.

On measuring the diameter of a reinforcement steel in a concrete, a sensor (not shown in the figure) is stepping along the straight-line path 7 from an end 8 of the concrete to the other end 9 while continuously detecting the magnetic field 6 of the concrete to obtain a continuous data. And, after a certain calculation, generate a line 51,52 representing the data on a display (not shown in the figure). Before obtaining the data line 52 shown in FIG. 4 by detecting the magnetic field 6 of the concrete, the magnetic field 6 of the concrete of the same kind yet with no reinforcement steel should be detected at first to obtain the data line 51 of the sole concrete (as shown in FIG. 3) for comparison. And then, a comparison is made between the data line representing the concrete with a reinforcement steel and that with no reinforcement steel so that the positions represented by the beginning point and the ending point of the differential part between the two data lines 51,52 can be obtained, where the beginning point and the ending point of the differential part represent two ends of a diameter of the reinforcement steel and so the diameter of the reinforcement steel can be obtained.

Although the apparatus according to the above prior art can measure the diameter of a reinforcement steel in a concrete, the construction is complex enough and, because of the sensor's measuring while stepping, the sensor is not easy to be set. Moreover, the data lines are obtained through a certain calculation and the diameter of the reinforcement steel in the concrete is obtained by comparing the two data lines so that much more calculations and comparisons are needed. In addition, the data obtained in this way is apt to be influenced by permeability, interval between reinforcement steels, etc. so that erroneous judgments may be increased. It is also hard to do an on-the-spot examination and evaluation with the above apparatus. So, the prior art does not fulfill all the requirements of the users on actual use.

SUMMARY OF THE INVENTION

Therefore, the main purpose of the present invention is to evaluate the size of a reinforcement steel and its defects by the size of a comparing element shown on a display unit so that the examination accuracy can be greatly improved and the examination result can be a reference to the safety of a construction.

The second purpose of the present invention is to be widely applied to examining the size of a reinforcement steel and its defects, which can also be the basis for evaluating the safety of a construction by examining the size of a reinforcement steel and its defects.

The third purpose of the present invention is to improve the examination accuracy with the help of comparing with a comparing element.

In order to achieve the above purposes, the present invention is a method and an apparatus for measuring the diameter of a steel reinforcement rod in a concrete. The apparatus according to the present invention comprises a comparing element, which is deposed outside of a to-be-examined construction and is corresponding to a reinforcement steel in the construction; a radioactive-ray source, which is located at a position capable of irradiating the comparing element and the reinforcement steel; and a display unit, which correspondingly located near the comparing element and the reinforcement steel where their magnifications are the same. The method according to the present invention comprises deposing a comparing element outside of a to-be-examined construction and corresponding the comparing element to a reinforcement steel in the construction; irradiating the comparing element and the reinforcement steel; and providing a display unit to show an image record of the comparing element and the reinforcement steel obtained by the irradiation of the radioactive-ray source. Accordingly, the size of the reinforcement steel and its defects can be evaluated by the size of the comparing element shown on the display unit so that the examination accuracy can be greatly improved and the examination result can be a reference to the construction safety.

BRIEF DESCRIPTION OF THE DRAWINGS

The present invention will be better understood from the following detailed descriptions of the preferred embodiments according to the present invention, taken in conjunction with the accompanying drawings, in which.

DESCRIPTION OF THE PREFERRED EMBODIMENT

The following descriptions of the preferred embodiments are provided to understand the features and the structures of the present invention.

Figure 1:
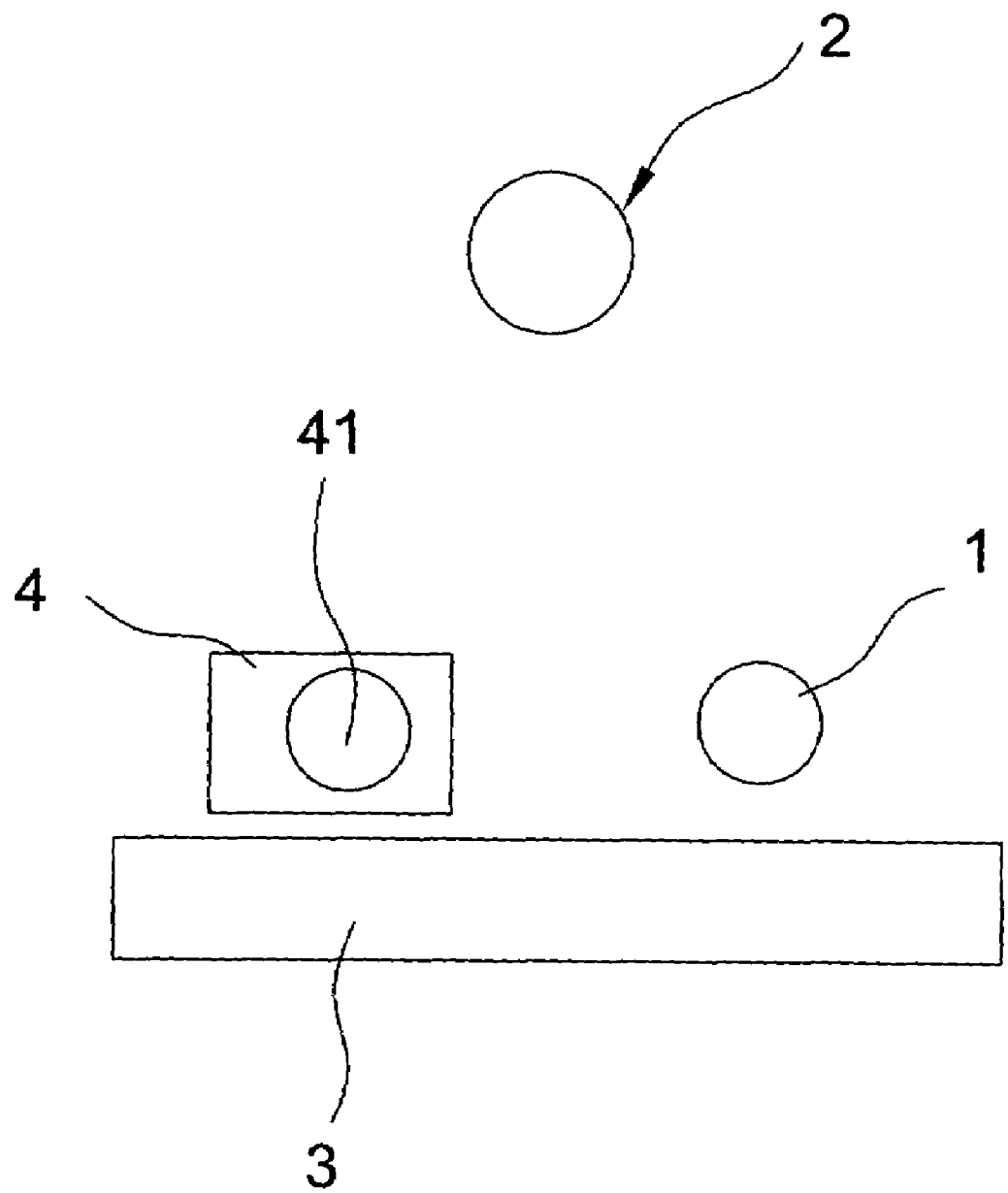
FIG. 1 is a view showing an apparatus according to the present invention.

Please refer to FIG. 1, which is a view showing an apparatus according to the present invention. As shown in the figure, an apparatus for measuring the diameter of a steel reinforcement rod in a concrete comprises a comparing element 1, a radioactive-ray source 2 and a display unit 3, where, by comparing with the size of the comparing element 1 displayed on the display unit 3, the size of a reinforcement steel in a construction can be estimated and its defects can be identified so that the examination accuracy is greatly enhanced to be a reference for evaluating the construction safety.

The comparing element 1 can be a circular globe deposed outside of a construction 4 and corresponding to a reinforcement steel 41 in the construction 4.

The radioactive-ray source 2 is deposed at a default position, where rays capable of penetration are produced and the comparing element 1 and the reinforcement steel 41 are irradiated by the rays.

The display unit 3 is correspondingly deposed at a position near the comparing element 1 and the reinforcement steel 41; and the display unit 3 can be a film or a monitor to generate an image record of the comparing element 1 and the reinforcement steel 41.

Figure 2:
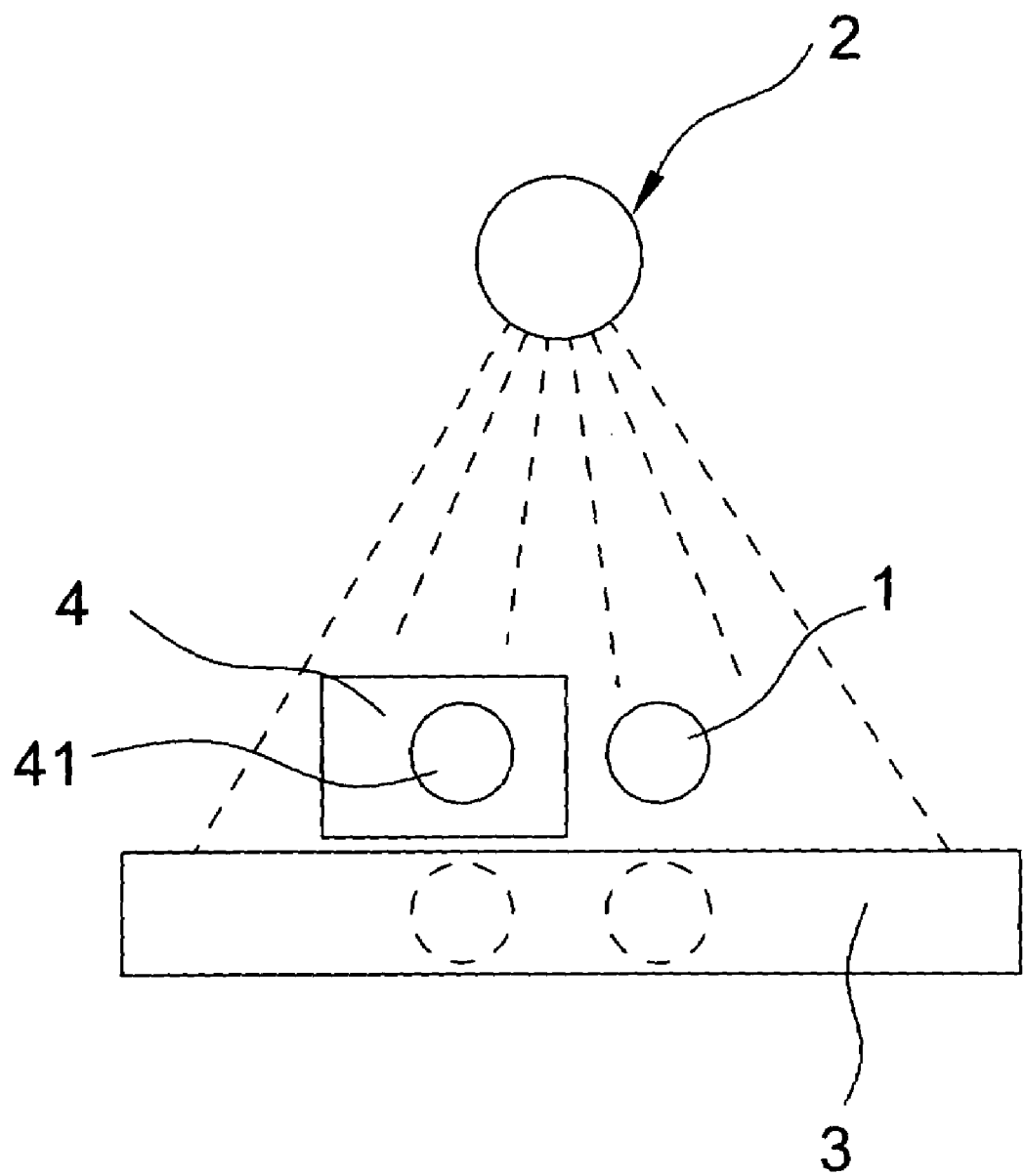
FIG. 2 is a view showing a status of use according to the present invention.
Figure 3:
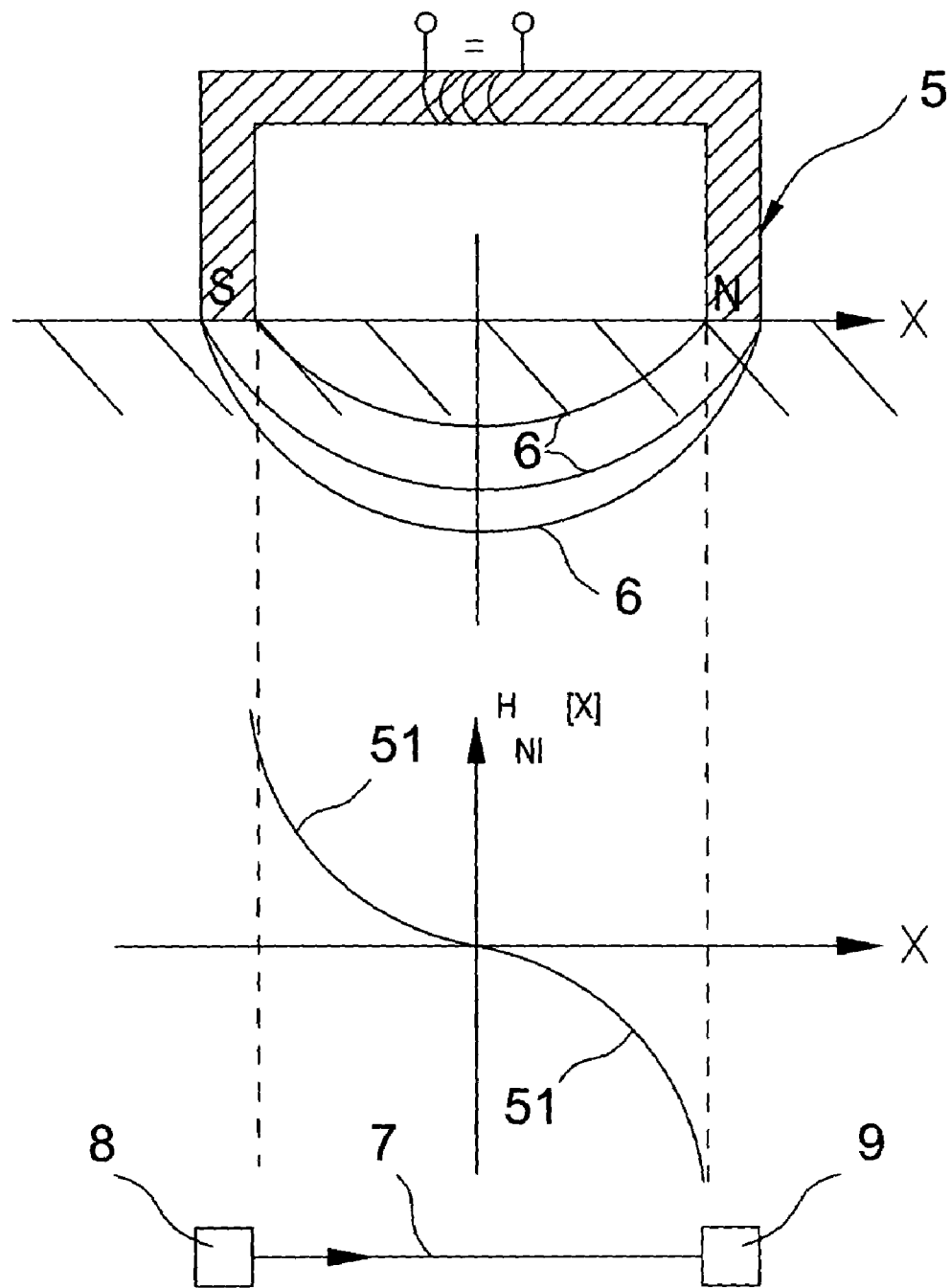
FIG. 3 is view showing a data line for a concrete without a reinforcement steel according to the prior art.
Figure 4:
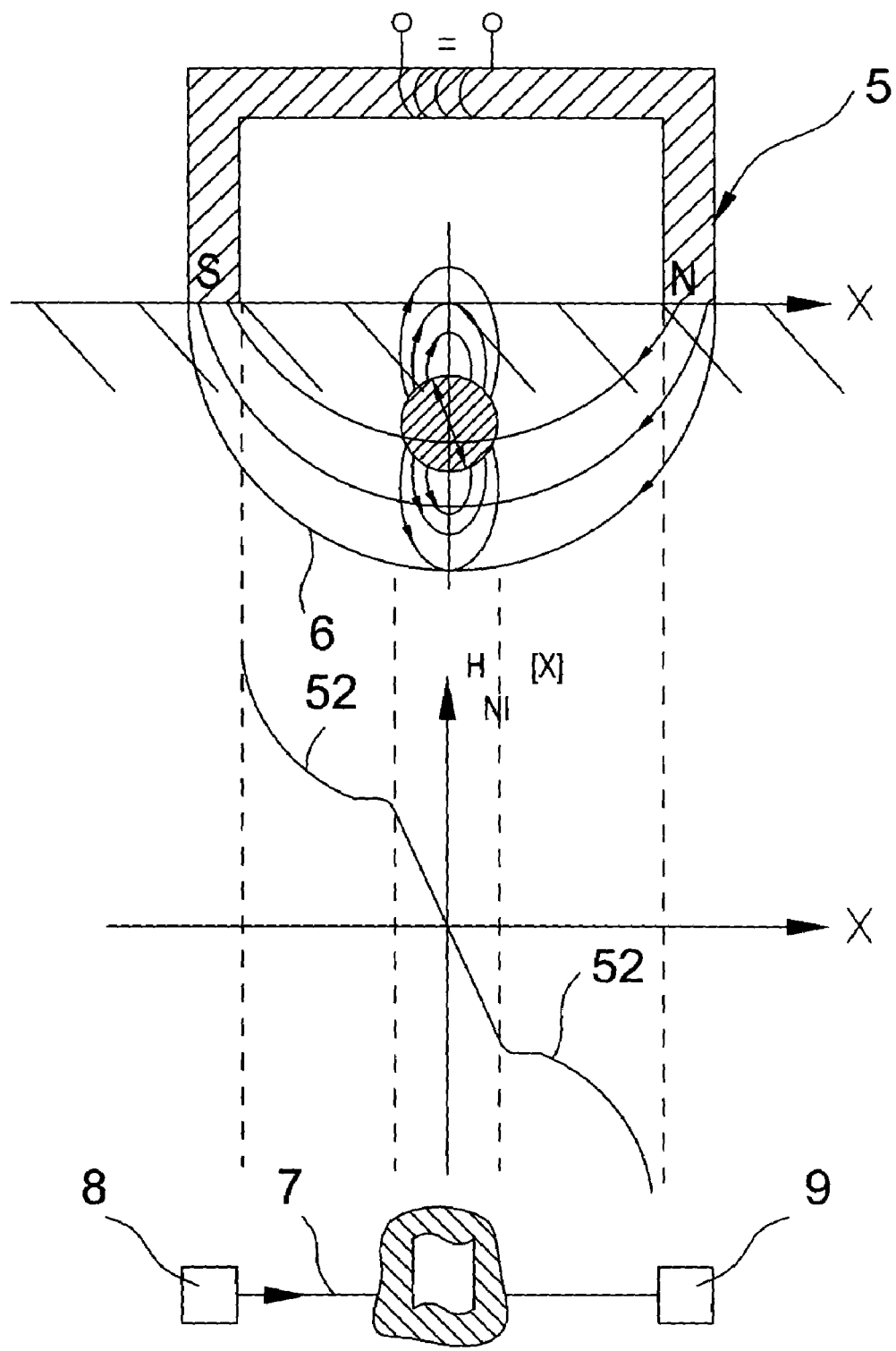
FIG. 4 is a view showing a data line for a concrete with a reinforcement steel according to the prior art.

Please refer to FIG. 2, which is a view showing a status of use according to the present invention. As shown in the figure, on using, obtain a comparing element 1 of a circular globe to be put outside of a to-be-examined construction 4 and corresponding to a reinforcement steel 41 in the construction 4. Then, irradiate the comparing element 1 and the reinforcement steel 41 with a radioactive-ray source 2 which can produce rays capable of penetration. Because the radioactive-ray source 2 is able to produce rays capable of penetration, a display unit 3 can be applied to show an image record of the comparing element 1 and the reinforcement steel 41, where the image record is obtained by the irradiation of the radioactive-ray source 2. And then, by the diameter size of the comparing element 1 displayed on the display unit 3, evaluate the size of the reinforcement steel 41 and its defects to be the basis for evaluating the construction safety. By doing so, with the help of comparing with the comparing element 1 of a circular globe, the present invention is advantaged in non-destructive examination, high sensitivity and full display so that the examination accuracy can be greatly improved.

To sum up, the present invention is a method and an apparatus for measuring the diameter of a steel reinforcement rod in a concrete, which can evaluate the size and the defects of a reinforcement steel in a construction by the size of a comparing element shown on a display unit so that the examination accuracy can be greatly improved and the examination result can be a reference for evaluating the construction safety.

The preferred embodiments herein disclosed are not intended to unnecessarily limit the scope of the invention. Therefore, simple modifications or variations belonging to the equivalent of the scope of the claims and the instructions disclosed herein for a patent are all within the scope of the present invention.

What is claimed is:

1. An apparatus for measuring the diameter of a steel reinforcement rod in a concrete, comprising:
   a comparing element deposed outside of a construction and corresponding to a steel reinforcement rod in said construction;
   a radioactive-ray source located at a position wherein said comparing element and said steel reinforcement rod are irradiated by said radioactive-ray source; and
   a display unit correspondingly deposed at a position near said comparing element and said steel reinforcement rod wherein the magnification of said comparing element and the magnification of said steel reinforcement rod are the same,
   wherein said comparing element is a circular globe.

2. The apparatus according to claim 1, wherein said radioactive-ray source produces rays capable of penetration.

3. The apparatus according to claim 1, wherein said display unit is a film.

4. The apparatus according to claim 1, wherein said display unit is a monitor.

5. A method for measuring the diameter of a steel reinforcement rod in a concrete, comprising the following steps of:
   a. obtaining a comparing element deposed outside of a to-be-examined construction and corresponding to a steel reinforcement rod in said construction;
   b. irradiating said comparing element and said steel reinforcement rod with a radioactive-ray source which produces rays capable of penetration; and
   c. providing a display unit to show an image record of said comparing element and said steel reinforcement rod, wherein said image record is obtained by the irradiation of said radioactive-ray source,
   wherein said comparing element is a circular globe.

6. The method for a measuring diameter according to claim 5, wherein said display unit is a film.

7. The method for a measuring diameter according to claim 5, wherein said display unit is a monitor.

* * * * *